United States Patent [19]

Gardiner

[11] Patent Number: 4,802,494
[45] Date of Patent: Feb. 7, 1989

[54] MEASUREMENT OF THE NEUTRAL ALIGNMENT POSITION OF THE FOOT

[75] Inventor: Roy J. W. Gardiner, Toronto, Canada

[73] Assignee: Sports Bio-Mechanics Research Inc., Toronto, Canada

[21] Appl. No.: 914,270

[22] Filed: Oct. 2, 1986

[51] Int. Cl.$^4$ .............................................. A61B 5/10
[52] U.S. Cl. ................................... 128/779; 128/782; 33/3 C; 33/512
[58] Field of Search .............. 128/774, 779, 781, 782; 73/172; 33/511, 512, 515, 3 B, 3 C

[56] References Cited

U.S. PATENT DOCUMENTS

| | | | |
|---|---|---|---|
| 2,017,813 | 10/1935 | Giuntini | 33/3 B |
| 2,095,268 | 10/1937 | Roberts | 73/172 |
| 2,255,066 | 9/1941 | Lamb | 128/25 B |
| 2,477,817 | 9/1949 | Mirti | 33/3 A |
| 2,795,953 | 6/1957 | Makowsky | 73/172 |
| 3,336,917 | 8/1967 | Pile et al. | 128/781 |
| 4,033,329 | 7/1977 | Gregory et al. | 128/781 |
| 4,492,236 | 1/1985 | Pile | 128/781 |
| 4,548,289 | 10/1985 | Mechling | 128/782 |

Primary Examiner—Kyle L. Howell
Assistant Examiner—Randy Citrin
Attorney, Agent, or Firm—Banner, Birch, McKie & Beckett

[57] ABSTRACT

An apparatus is disclosed having a toe support portion, an arch support portion and a heel support portion, each of which are mounted along a longitudinal axis to be aligned with the elongate dimension of the foot, so as to be engageable with the respective portions thereof. The supports are movable along a vertical axis and rotatable about the longitudinal axis. A displacement means is also provided in coupling engagement with each support portion to displace vertically one of the support portions in response to vertical displacement of another of the support portions. A method is also disclosed for determining the neutral alignment position of a foot, while a further method is provided for ascertaining the condition of the posture of a person.

18 Claims, 4 Drawing Sheets 4,802,494

MEASUREMENT OF THE NEUTRAL ALIGNMENT POSITION OF THE FOOT

This invention relates to an apparatus for determining the neutral alignment of the foot.

BACKGROUND OF THE INVENTION

The human foot consists of numerous different bones. These bones, in conjunction with numerous muscles and ligaments, distribute the body's weight on the ground. For each foot, there is a neutral alignment position. In this position, the various bones are aligned properly, and the various muscles and ligaments are not unnecessarily tensioned. However, for some feet in the neutral alignment position, the bottoms thereof are not horizontal. Moreover, the toe and heel might not be coplanar. When moving about, as by running or walking, on an uneven surface, this is of little consequence. To accommodate the variations in the surface, each foot is randomly deflected by small amounts. As a consequence, the various muscles and tendons are more or less uniformly stretched.

However, for many people, most everyday movement is carried out on a substantially flat surface. Thus, for people living in an urban environment, nearly all surfaces on which they walk are horizontal with little unevenness. Also, for athletes, many playing or exercise surfaces are also horizontal. As a result, if a foot has a non-horizontal neutral alignment position, then when weight is placed on the foot it has to adopt a "compensated" position. In other words, the foot compensates, so that its bottom surface is horizontal. In the compensated position, ligaments can be stressed and imbalances set up in various muscles, the degree of stress and muscle imbalances being proportional to the degree of compensation. This can also effect the amount of flexibility.

It has also been realized that maintaining proper neutral alignment of the feet is important, since the various components of the human skeleton are related, and stress set up in one part of the skeleton can effect numerous other parts. Thus, the continuous maintenance of the feet in compensated positions can lead to stress and problems in not only the feet themselves, but also in the legs, knees, lower and upper back and neck.

For athletes, a large number of injuries are caused by stress from over-use or due to a limited amount of flexibility. It is believed that by stabilizing the feet into neutral alignment positions and reconditioning the body to a balance of strength and flexibility, greater endurance can be achieved.

Accordingly, it is desirable to obtain neutral alignment in a person's foot. However, the problem arises of accurately determining the neutral alignment position of the foot. Present techniques are somewhat crude and ineffective.

In one technique, a goniometer or tractograph is used. The foot is placed in a non-weight bearing position, and palpitated to align the bones. To a large extent, the measurements rely upon the judgment of the person taking the measurements. Moreover, such measurements are determined from simple visual observation.

Other techniques take measurements in a weight bearing condition by the taking of an imprint of the foot. However, these measuring techniques do not permit free, unrestricted movement of the foot in all three planes which is a particularly important factor in the accurate determination of the neutral alignment position. Furthermore, these rudimentary measurements become the basis for the preparation of an orthotic which compensates the foot by allowing for separate misalignment of the heel and the toe. However, due to the inaccuracies in the current measuring processes, many orthotics still result in residual misalignment of the foot.

It has been realized that it is desirable to achieve an accurate measurement of the neutral alignment position of the foot. Such a measurement should not rely excessively upon the judgment or experience of the person taking the measurements. Further, to achieve accurate measurements of the neutral alignment position, these measurements should be taken in a load or weight bearing position, with the foot free to move in certain directions.

It is therefore an object of the present invention to obviate or mitigate the above-mentioned disadvantages by providing a novel technique of measuring the neutral alignment position.

In accordance with the present invention, there is provided an apparatus for determining the neutral alignment position of the toe, arch and heel portions of the foot, comprising:

a toe portion support means, an arch portion support means, a heel portion support means, each of the support means being mounted along a longitudinal axis to be aligned with the elongate dimension of the foot, so as to be engageable with the respective portions thereof, each of the support means being movable along a vertical axis and rotatable about at least the longitudinal axis, and displacement means coupled with each of the support means to displace vertically one of the support means in response to vertical displacement of another of the support means.

A method is also provided for determining the neutral alignment position of the foot of a person using a device comprising a toe portion support means, an arch portion support means, a heel portion support means, each of said support means being mounted along a longitudinal axis to be aligned with the elongate dimension of said foot so as to be engageable with the respective portions thereof, each of said support means being movable along a vertical axis and rotatable about at least said longitudinal axis, and displacement means coupled with each of said support means to displace vertically one of said support means in response to vertical displacement of another of said support means, aligning the toe, arch and heel portions of a foot on the respective support means, orienting the person so as to place said foot in a body weight bearing condition, so as to apply a pressure distribution over said support means, said pressure distribution causing said foot to assume a neutral alignment position by way of relative displacements of said support means with respect to said vertical axis, and rotations of said support means with respect to said longitudinal axis, and observing the results of said displacements and rotations, so as to determine said neutral alignment position A further method is provided for ascertaining the kinesic condition of a person comprising the steps of:

placing the feet of said user on respective ones of two assemblies, each of said assemblies comprising a toe support, an arch support and a heel support respectively, said supports in each assembly being disposed along a longitudinal axis and displaceable with respect to a vertical axis, rotatable about a longitudinal axis and collectively rotatable about said vertical axis, orienting said person to a position wherein said feet are in a body weight bearing condition, causing a pressure distributions to be applied over said supports, said pressure distribution causing relative vertical displacement between said supports to balance said pressure distribution for each foot, said vertical displacement being governed by a relationship between said supports, whereby displacement of one of said supports causes a compensating displacement of at least one of said other supports, said pressure distribution also causing rotation of at least said heel and toe supports about said longitudinal axis to balance said pressure distribution over the respective support, and the collective rotation of said supports in at least one of said assemblies about a vertical axis so as to accommodate torsional imbalances between the foot, the leg and the hip portion of said person, said vertical displacements supports causing each of said feet to assume a neutral alignment position, causing vertical displacements of said toe, arch and heel portions from said neutral alignment position toward displacement limits in each direction therefrom, measuring said displacements so as to determine said displacement limits, causing rotation about said longitudinal axis of said toe, arch and heel portions from said neutral alignment position toward limits of longitudinal rotation in each sense therefrom, measuring said rotations so as to determine said limits of rotation, causing collective rotation of said supports for at least one of said feet from said neutral alignment position toward limits of collective rotation about said vertical axis in each sense therefrom, measuring said collective rotations so as to determine said collective rotation limits, said limits of displacement and rotation being indicative of ranges of motion in each of three dimensions.

Thus, the present invention involves the measurement of the neutral alignment position while the foot is in a load bearing position, and thereby provides a more accurate determination of the neutral alignment position than those devices presently known. Furthermore, the present invention enables the analysis of the bone alignment as well as muscle and ligament imbalance by providing a technique for determining ranges of motion of the various portions of the foot as well as the leg and hips.

The term "neutral alignment position" refers to an equilibrium position of the foot in a weight bearing condition in which the bones are aligned and the muscles and ligaments are balanced. This position is identifiable in any body configuration, wherein each foot assumes a particular position depending on the body weight exerted on the foot and the shape of the ground surface, and in such a position cooperates with the bones, muscles and ligaments in the rest of the body to provide the most efficient use of energy in transferring forces to the ground.

BRIEF DESCRIPTION OF THE DRAWINGS

For a better understanding of the present invention, and to show more clearly how it may be carried into effect, reference will now be made, by way of example only, to the accompanying drawings, which show several embodiments of the present invention, in which.

DETAILED DESCRIPTION OF THE PREFERRED EMBODIMENTS

Figure 1:
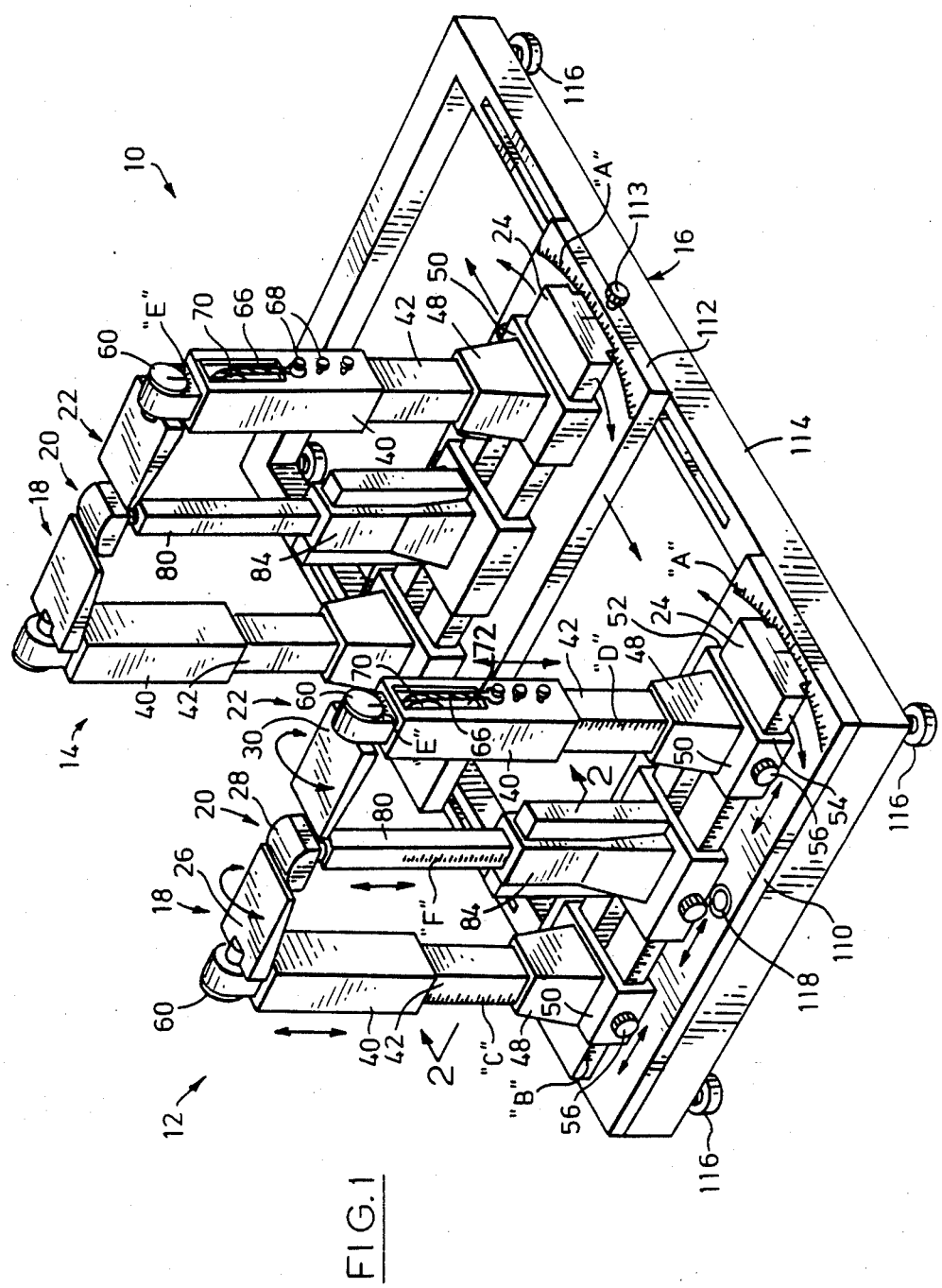
FIG. 1 is a perspective view from above a neutral alignment measuring device.
Figure 2:
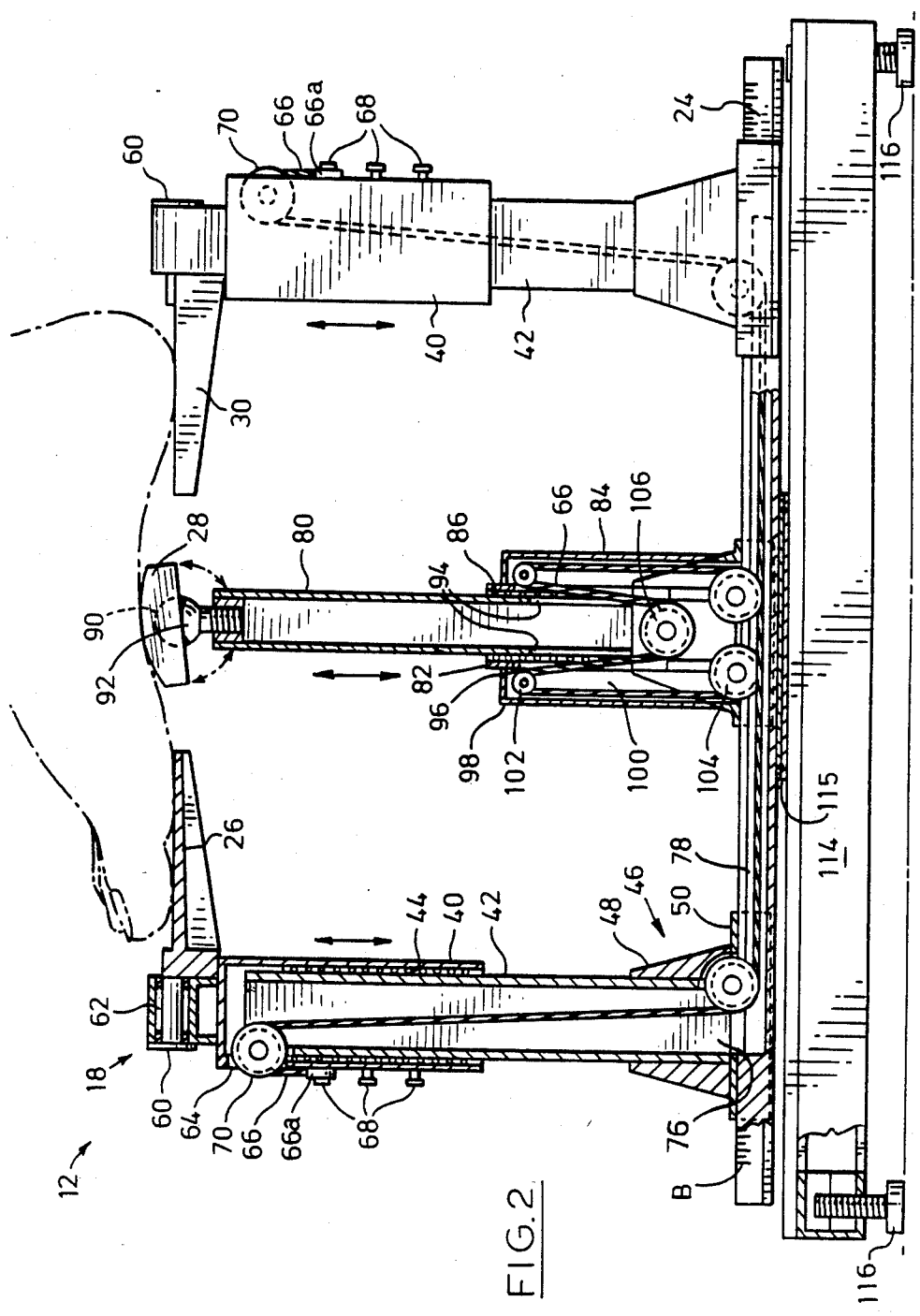
FIG. 2 is a side view, in partial section, along the line 2—2 of FIG. 1.

Referring to FIGS. 1 and 2, the neutral alignment measuring device 10 includes a pair of foot support assemblies 12, 14 rotatably mounted on a base assembly 16 with the degree of rotation being identified by gradation markings "A". Each foot assembly has three support portions, a toe support portion 18, an arch support portion 20 and a heel support portion 22, each support portion being adjustably mounted on an elongate element 24 and movable therealong. The displacement of each of the support portions is indicated by way of gradation markings "B".

Receiving the toe, arch and heel portions of the foot respectively are toe, arch and heel plates 26, 28, 30 respectively, which are rotatably mounted in the upper region of the respective support portions. Each of the toe and heel support portions 18, 22 respectively has an outer sleeve 40 which is vertically slidable on a rectangular tubular column 42, with sliding friction being minimized by the use of ball bearings as is shown at 44. The displacement of the sleeves is indicated by the gradation markings "C" and "D".

The tubular column 42 is vertically positioned in a bracket 46 which is formed of a column portion 48 receiving the lower end of the column 42, and a guide portion 50. The guide portion 50 includes a pair of downwardly extending right angled arms 52, 54 which slidably engage the lateral extremity of the elongate member 24. The brackets are releasably positioned along the elongate member by way of a threaded member 56. As with the heel plate 30, the toe heel plate is rotatably mounted on the upper end of the sleeve 40 by way of a shaft 60, with the rotation friction being minimized by needle bearings identified at 62. Rotation of the toe and heel plates are each indicated by the gradation markings "E".

Formed in the upper region of each of the sleeves is an elongate aperture 64 through which extends a cable 66, the end 66a of which is releasably coupled to one of a number of holding pins 68 aligned on the outer surface of the sleeve. Also extending through the aperture is an upper pulley 70 which is mounted near the upper end of the column through an aperture 72 formed therein. The column also has an aperture 74 formed in the lower end thereof which cooperates with apertures 76 formed in both the guide portion 50 and a channel 78 formed in the central region of the elongate member 24.

The arch support portion 20 also includes a tubular column 80 telescopingly engaged in a sleeve 82, with movements of column 80 being registered by gradation markings "F". In this case the sleeve 82 is vertically positioned on a bracket 84, and ball bearings 86 are provided between the tubular column 80 and the bracket 84 to reduce sliding friction. The arch plate 28 has a socket 90 formed in the lower surface thereof which engages a spherical element 92 mounted in the upper end of the tubular column 80.

The tubular column 80 also has a pair of elongate apertures 94, 96 formed in opposite sides thereof, and are adjacent elongate apertures 94 formed in the bracket. Enclosing the elongate apertures 96 are housings 98 which define an inner cavity 100, each having a pulley 102 mounted in the upper region thereof. The pulleys 102 are each located above a pulley 104 mounted in the lower region of the bracket, and extends into the channel 78 formed in the elongate member 24. Pulleys 104 direct the cable 66 from the channel 78 and through the housing to a central pulley 106 mounted on the lower end of the column 80.

In this manner a continuous cable is entrained on a multiple pulley configuration and interconnects each of the toe, arch and heel support portions 18, 20, 22. Thus, any displacement of one of the support portions will cause a proportional reaction displacement by the other support portions, with the reaction displacement being dependent on the force distribution on each of the toe, arch and heel plates 26, 28, 30 respectively as will be described.

Each of the foot support assemblies is respectively pivotally mounted on plate elements 110 and 112, by way of a bearing identified at 114. The plate element 110 is fixed to the base 114. The plate element 112 is rollable along the base 114 by way of a bearing assembly (not shown) to enable the foot support assemblies 12, 14 to be spaced relative to one another in accordance with the particular dimensions of the user. The plate 112 is also lockable into position by way of threaded fastener 113. The base is also provided with height adjustable legs 116 and a level bubble 118 to ensure proper horizontal orientation of the neutral alignment measuring device 10.

To operate the device 10, the foot support assemblies 12 and 14 are first separated along the base assembly 16 by way of displacing plate element 112 with respect to base 114, at a distance corresponding approximately to the distance between the shoulders of the user. The threaded fastener 113 is then turned to fix the foot support assembly in position with respect to the base 116.

The user then stands on the foot support assemblies 12, 14, with the toe, arch and heel portions of the feet being aligned with the respective plates 26, 28 and 30. By virtue of the fact that the plates are free to rotate as above-mentioned, pressure variations along the plates will cause each plate to rotate until an equilibrium position is reached where the force is balanced on each side thereof. In addition, variations in vertical forces between the toe and heel support portions cause each of them to displace vertically until the forces are balanced while maintaining a pressure on the arch.

The relative vertical displacement of the plates is dependent on the cable 66 and pulleys, since notation of one pulley, for example pulley 70 of the toe support portion 18, requires a compensating notation of the equivalent pulley in the heel support portion 22 and the pulley 106 of the arch support 20. This is due to the fact that the length of the cable does not change to any discernable degree. Thus, any unbalanced downward force on the toe support plate 28 will cause a downward displacement thereof and an upward displacement of the heel support plate 30 and perhaps a relatively smaller upward displacement of arch support plate 28 until the downward force is counterbalanced by the tension in the cable 66.

In addition, any natural tortional misalignment of the feet with respect to the respective legs and hips of the user is registered by rotation of the foot support assemblies 12, 14 with respect to the plate elements 110, 112 respectively.

The neutral alignment position is then reached when the device has accommodated to the force and pressure on balances of the various support plates and may be recorded by measuring the various displacements by way of the gradation markings "A" through "E".

It is to be noted that although the apparatus 10 provides a measurement of the neutral alignment position of each foot, the apparatus may be used in a variety of other procedures, each of which contributes to the overall analysis of the conditions of bones, muscles and ligaments of the users body, as will be later described.

Figure 3:
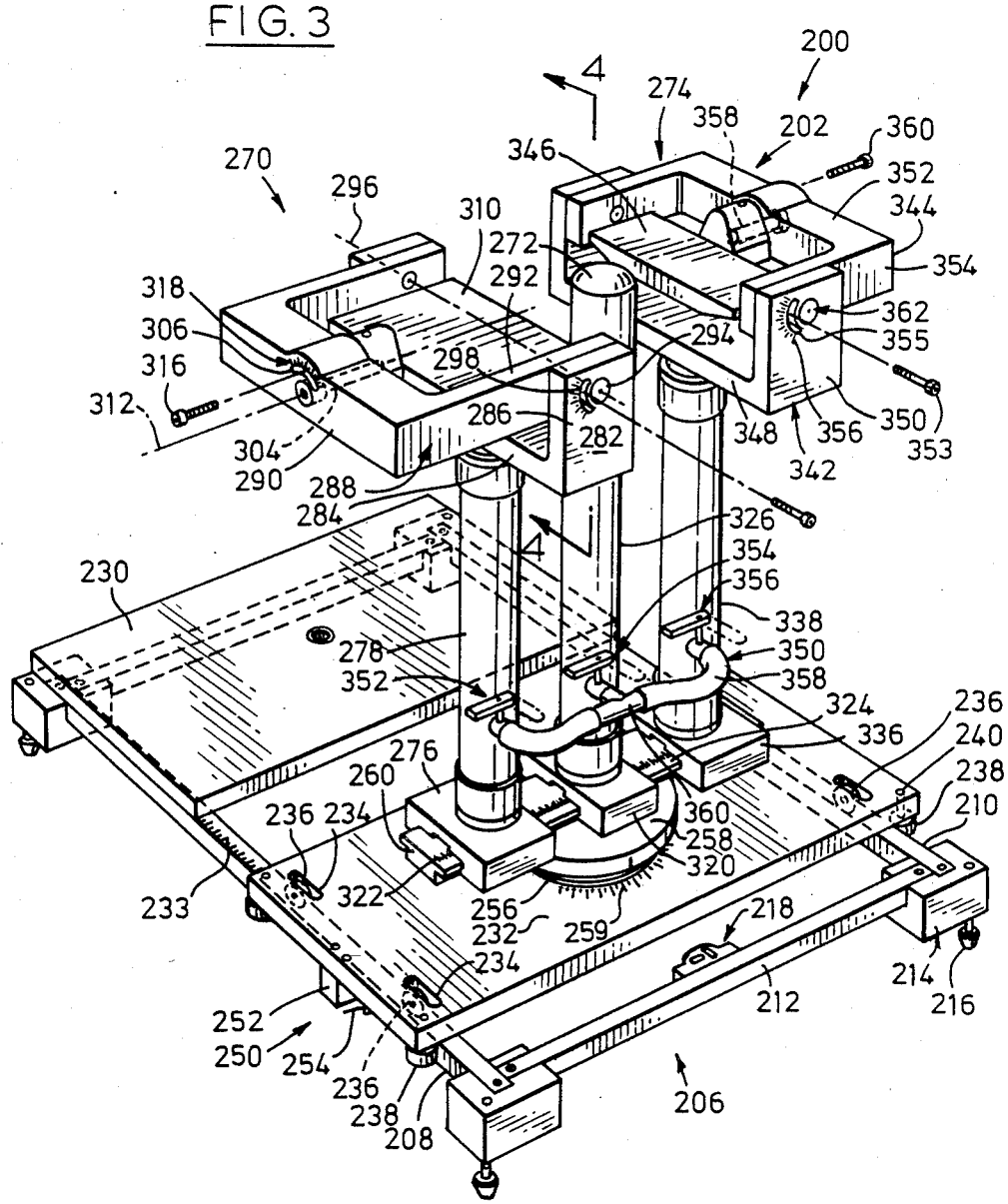
FIG. 3 is a downward perspective view of an alternative neutral alignment measuring device.
Figure 4:
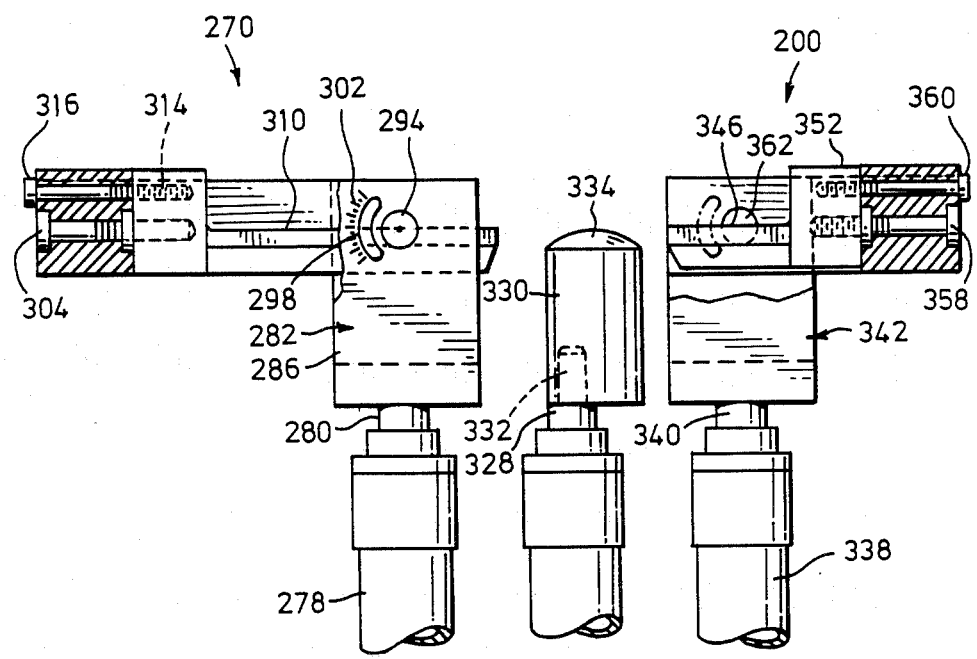
FIG. 4 is a side view of a partial section taken along line 4—4 of FIG. 3.

Referring now to FIG. 3, an alternative alignment measuring device as a whole is denoted by the reference 200. The alignment measuring device 200 comprises a pair of identical foot support assemblies, the left foot support assembly being identified at 202. The right foot assembly is substantially identical to the left foot assembly 202, but is not shown for the sake of clarity and brevity.

The alignment measuring device 200 includes a base 206, formed by front and rear bars 208, 210, together with side bars 212, which are received in corner blocks 214.

Extending from each corner block 24 is an adjustable supporting pad 216. Located on the side bar 212 is a bubble level 218 which enables the base to be levelled by adjusting the supporting pads 216.

The right foot support assembly is mounted on a rectangular right-hand base plate 230 secured to the right-hand end of the base 206 by way of screws, bolts or the like.

The left foot support assembly is mounted on a left-hand base plate 232 which is mounted for transverse movement on the base 206 as indicated by graduated scales identified at 233. For this purpose, the base plate 232 includes four generally elongate openings 234, which are located above the front and back bars 208, 210. In each opening 234, there is located a horizontal roller 236 mounted on a respective shaft which is secured in the base plate 232. The rollers 236 are so mounted as to extend below the plate 232 and engage the upper surface of the front and rear bars on 208, 210 and thereby support the base plate 232.

To align the base plate 232 in a horizontal plane along the base 206, guide rollers 238 are provided. These guide rollers 238 are mounted for rotation about vertical axes and are mounted on a respective shaft 240, which is secured in the base plate 232 to engage the outer vertical surfaces of the front and back bars 208, 210. It will thus be seen that the arrangement of the roller 238 enables the base plate 36 to travel transversely between the right-hand base plate 230 and the left-hand corner blocks 214.

To lock the left-hand base plate 232 in position, a locking unit 250 is provided. The locking unit 250 comprises a block 252, secured to the base plate 232 and extending below the front bar 208. The locking unit 250 includes a Jergens threaded handle 254, which engages a threaded bore in the block 252 to clamp the plate 232 to the front bar 208.

The left foot support assembly 202 is rotatably mounted on the base foot plate 232 by means of a bearing 256, which supports a metal disc 258, with pivotal displacement being registered by a graduated scale shown at 259. An elongate element 260 is mounted on the metal disc 258 and has a generally T-shaped section, with the vertical limb of the T-shape forming the major part of the section.

The left foot support assembly 202 includes a toe support portion 270, an arch support portion 272 and a heel support portion 274. It is to be noted that, as for the toe support portion 18, the designation "toe" is used to represent not only the toes but also the forward ends of the metatarsus.

The toe support portion 270 has a bracket 276, mounted for sliding movement along the elongate element 260. A hydraulic cylinder 278 extends vertically upward from the bracket 276, and includes a piston 280 which supports a first toe support bracket 282. This support bracket 282 has a horizontal cross piece 284 and two upwardly extending arms 286. A second toe support bracket 288 includes a cross piece 290, and two arms 292 which extend horizontally and rearwardly from the cross piece 290. The arms 286, 292 are connected together for pivotal movement by way of pivot shafts 294 which define a transversely extending pivot axis 296. To lock the two brackets together, one arm 286 includes an arcuate slot 298 in line with threaded bore is provided in the adjacent arm 292. A bolt 300 extends through the slot 298 and engages the threaded bore, which can then be used to clamp the pair of arms 286, 292 together so as to lock the brackets 282, 288 relative to one another. A scale 302 is provided around the arcuate slot 298, while the bolt 300 is such as to provide an accurate indication of the angular position between the brackets 282, 288.

The cross piece 290 of the second toe bracket 288 includes a bore 304, and above the bore 304 an arcuate slot 306, formed in a raised part of the cross piece 290. Extending through the bore 304 and beyond the inner surface of cross piece 290 is a shaft onto which is pivotally mounted a toe support platform 310 for pivotal movement about a longitudinal axis relative to the second toe bracket 288. This axis is indicated at 312.

The platform 310 includes a threaded bore 314, in which a bolt 316 is received. Again, this enables the platform 310 to be secured relative to the second toe bracket 288. A scale 318, corresponding to the scale 302 is provided around the arcuate slot 306, for measuring the angular position of the support platform 310.

Located at the center of the elongate element 260 is a center bracket 320, which defines a central reference for the longitudinal position of the toe and heel support portions 270, 274 to enable the relative position of the toe and heel support portions 270, 274 to be measured, two scales 322, 324 are provided extending outwardly from the centre bracket 320. A central hydraulic cylinder 326 extends upwardly from the central bracket 320 and includes a piston 328. A central arch support body 330 is mounted on the piston 328 by way of an eccentrically located bore 332 engaging the upper end of piston 328 of a reduced diameter. The body 330 is generally cylindrical with a domed top surface 334, for supporting the arch of the user's foot. The arch support body 330 can be freely rotated about the piston 328 to a desired position. As an alternative, the pivotal arrangement provided by the piston 328 can be replaced by a ball and socket joint as in the previous embodiment.

The heel support portion 274 includes a rear sliding bracket 336. A hydraulic cylinder 338 extends upwardly from this sliding bracket 336, and has a piston 340, on which is mounted a first heel support bracket 342. The heel support bracket 342 supports a second heel support bracket 344, and a heel support platform 346, the arrangement of these components generally corresponding to that for the toe support portion 270.

The first heel support bracket 342 includes a cross piece 348 and upwardly extending arms 350. The second heel support bracket 344 correspondingly has a cross piece 352 and arms 354. Short pivot shafts 362 pivotally connect the arms 350, 354 together.

Again, a locking arrangement is provided by a bolt 353 engaging a bore of an arm 354 and passing through an arcuate slot 355 formed in arm 350. A corresponding angular scale is also provided, and this arrangement is indicated at 356.

Heel support platform 346 is pivotally mounted by a shaft in a bore of the cross piece 352, as indicated at 358, while a locking arrangement and angular position measuring device is provided by a bolt 360.

The pivot shafts 362 form a transverse horizontal pivot axis whilst the shaft 358 provides a longitudinal horizontal pivot axis for the heel support platform 346.

For both the toe support platform 310 and the heel support platform 346, the respective axes extend through the centre of a top planar surface of the platform. These axes thus lie in the planar surface of the platform, when the respective platform is horizontal. This prevents torques or moments being developed by the load applied by a user's foot. Each platform 310, 346 should thus pivot freely, so as to uniformly support a person's foot.

As shown most clearly for the heel support platform 346, it is cast or otherwise formed in one piece. It is of generally uniform thickness at the center and tapers toward the edges. The toe support platform 310 is of a similar configuration, but longer, so as to accommodate the metatarsus.

The hydraulic cylinders 278, 326 and 338 are interconnected by way of a hydraulic coupling generally identified at 350. The hydraulic cylinders 278, 326 and 338 have bores formed in the side wall thereof into which is respectively threadedly engaged hydraulic valves 352, 354 and 356. The outlets of the valves 354, 356 are interconnected by hoses 358, which are joined to a "T" coupling shown at 360. Each of the valves has an "open" position as shown in solid lines and a "closed" position as shown in dashed lines. The hydraulic coupling 350 provides a closed circuit between cylinders 278, 326 and 338, so that downward movement of one of the cylinders, for example cylinder 278, results in compensating upward movement of one or both of the other cylinders, that is cylinders 326, 338, depending on the pressure variations therebetween.

Furthermore, if the hydraulic cylinders 278, 326, 338 are dimensionally equivalent, the compensating upward movement of one of cylinders 326, 338, or the sum of the upward movements of cylinders 326 and 338 equals the downward movement of cylinder 278.

In addition, valves 352, 354, 356 may be used to isolate one of the three cylinders from the others. This is particularly useful to prevent displacement of the arch support portion 272 so as to determine the relative movement of the toe and heel support portion 310, 346. Further, for some applications, it may be desirable to provide hydraulic cylinders of different sizes, thus effectively altering the relative displacements of the cylinders and the proportion of the load taken by each cylinder.

A description will now be given of the use of the alignment measuring device.

First, the handle 254 is operated to release the left measuring apparatus 202. The toe and heel support portions 270, 274 are then adjusted to the approximate size of the user's foot. The user then steps onto the left and right measuring apparatus 202, 204. The user's feet will either be bare, or lightly clad by socks, etc. so that they can readily assume their neutral, aligned positions. It may be desirable to provide a steadying bar or the like, to assist a user in stepping onto and off the measuring device 200.

Once the user is standing on the two measuring apparatus 202, 204 with his weight fully taken by them, minor adjustments are made to ensure that his feet are properly held by the apparatus. Thus, the user can rotate his feet about vertical axes, due to the bearings 256, to assume a comfortable position. Similarly, he can move his feet to a comfortable transverse spacing, by rolling the left measuring apparatus 202 on its rollers 236. Once this position has been reached, it can be locked by means of the handle 254.

The position of each of the user's feet on the respective measuring apparatus 14 may then be accurately adjusted. In so doing, the arch support body 330 is rotated for correct positioning beneath the arch of the user's foot. Each of the toe and heel support portions 270, 274 is moved along the slide bar 260 until the toe and heel of each of the user's feet is fully engaged on the respective one of platforms 310, 346.

In the level positions of the platforms 310, 346 the various horizontal axes pass through the planar top surfaces of the respective platforms as above described. Consequently, each support platform 310, 346 will pivot about its respective pair of axes to provide a uniform support to the foot.

With the feet uniformly supported, the angular displacements of the platforms 310, 346 about their horizontal axes are then measured. This can either be carried out with the platforms still free to pivot, or with them secured, although it is preferable to secure both in position before taking these angular measurements. For this purpose, the bolts 300, in the toe support platform 310 and the corresponding bolts 353, for the heel support platform 346 would be tightened, whilst the user maintains his feet in the neutral aligned position. The readings of the various scales are then taken, to indicate not only the neutral alignment position but also the angular orientation of the left and right feet as well as the separation between them.

It should be noted that the vertical displacement, horizontal axis rotation and vertical axis rotation capabilities enable the foot to move in three dimensions. Furthermore, the placement of the user on the apparatus in the standing position enables this movement to occur, while the feet and legs are in a weight bearing position. Thus, the apparatus 10, 200 not only provide the static measurement of the neutral alignment position but also other analyses which are dynamic in nature.

For example, the apparatus 10, 200 may also be used to ascertain the condition of the posture of a person, by enabling various ranges of motion to be measured for the toe, arch and heel portions of the foot. This is done by causing displacement of each portion in the vertical direction from the neutral alignment position toward upper and lower boundaries. This analysis also involves rotating the portions of the foot about the longitudinal and vertical axis toward longitudinal and vertical rotation boundaries.

Imbalances in muscles or ligaments, and misalignment of bones may then be determined by the nature of the vertical displacements, for example by unequal displacements toward the boundaries.

In this procedure, the user's feet are aligned on the foot support assemblies in the above described manner, with the user orienting himself in the proper configuration. This configuration will depend on the particular field of analysis, and varies from full standing position to a crouched position, as is typical in the sport of skiing With the neutral alignment position obtained for the given body configuration, the boundaries of displacement of the various portions of the feet relative to the vertical axis as well as the boundaries of rotation in both the horizontal and vertical axis from the neutral alignment position may be determined. Each foot may then be measured from the neutral alignment position with respect to the three dimensions. Furthermore, the procedure may be carried out in three dimensions simultaneously or with the movement restricted to one or two dimensions.

With these measurements, bone misalignment, muscle or ligament imbalance and inflexibility in the legs, hip and lower back can be pinpointed.

This information is particularly important for not only correction of injuries causing such weaknesses, but also for prevention of injuries. This is due to the fact that inflexibility of a particular part of the body indicates susceptibility of that part to injury.

Also contemplated is the use of an electric circuit to measure the various displacements automatically and to present to the user a numerical representation of the neutral alignment position.

Thus, the present invention enables the measurement of the neutral alignment position of each foot, in an independent manner, while each foot is supporting its normal proportion of body weight. With such measurements, orthotics may then be prepared to orient the foot to its neutral alignment position.

I claim:

1. An apparatus for establishing the neutral alignment position of a foot, comprising:
    a toe portion support means,
    a heel portion support means and an arch portion support means disposed between said toe portion support means and said heel portion support means,
    connecting means for connecting said toe, heel, and arch portion support means together,
    each of said support means being alignable with the corresponding portions of said foot and mounted for relative movement parallel to a vertical axis and about a longitudinal axis in response to forces exerted thereon by said corresponding portions, and
    indicating means for indicating the orientation of each of said toe portion support means, said arch portion support means and said heel portion support means.

2. The apparatus as defined in claim 1 further comprising compensating means for compensating forces appearing on one of said toe support means and said heel support means in response to a variation in forces appearing on the other of said toe support means and said heel support means.

3. The apparatus as defined in claim 2 wherein said compensating means includes displacement means coupled with said toe support means and said heel support means for vertical displacement of one of said support means in response to vertical displacement of the other of said support means.

4. The apparatus as defined in claim 3 wherein said support means are each mounted on a support element and at least two of said support means are movable along said support element relative to the other along said longitudinal axis.

5. The apparatus as defined in claim 4, wherein said support element is rotatably mounted on a base.

6. The apparatus as defined in claim 5 further comprising register means for registering rotation of said frame portion relative to said base.

7. The apparatus a defined in claim 3 wherein each of said support means includes a platform means rotatably mounted to an extensible support member with respect to said longitudinal axis.

8. The apparatus as defined in claim 7 wherein said extensible support member includes a column portion and a sleeve portion telescopingly engaged and vertically slidable relative to said column portion.

9. The apparatus as defined in claim 8 wherein said displacement means includes pulley means rotatably mounted on each of said support members and cable means entrained on said pulley means for extension of one of said support members in response to retraction of another of said support members.

10. The apparatus as defined in claim 9 wherein said cable means has a pair of ends, each of which is mounted on respective ends of said extensible support members of said toe portion support means and said heel portion support means.

11. The apparatus as defined in claim 9 wherein said sleeve portions of each of said toe and heel portion support means includes adjustable mounting means for varying the relative displacement of said support means.

12. The apparatus as defined in claim 7 wherein said platform means of said arch portion support means is defined by an arch pad pivotally mounted on said extensible support member.

13. The apparatus as defined in claim 12 wherein said arch pad has formed therein a socket for slidable engagement with a ball portion formed on said extensible support member.

14. The apparatus as defined in claim 3 wherein said displacement means includes a hydraulic actuating circuit.

15. The apparatus as defined in claim 15 wherein said hydraulic actuating circuit includes a hydraulic ram coupled with each of said support means and a fluid coupling means interconnecting said rams, such that displacement of one of said rams causes a proportional displacement by the other of said rams.

16. The apparatus as defined in claim 1 wherein said indicating means includes register means for registering relative vertical displacement and rotation of said support means 17. An apparatus for establishing simultaneously the neutral alignment position of a left foot and a right foot of a user, comprising:
   a base,
   left and right foot support assemblies,
   each of said foot support assemblies supported on said base having a toe portion support means, a heel portion support means, and an arch portion support means disposed therebetween,
   said toe portion support means, said heel portion support means and said arch portion support means being adjustable relative to each other in order to align with the corresponding portions of the corresponding foot,
   each of said support means of a respective foot support assembly being mounted for relative displacement parallel to a vertical axis and about a longitudinal axis in response to forces exerted thereon by said corresponding portions, and
   indicating means for indicating the orientation of each of said toe portion support means, said arch portion support means and said heel portion support means.

18. The apparatus as defined in claim 17 wherein at least one of said foot support assemblies is rotatable on said base.

* * * * *